United States Patent
Ganapathy et al.

(10) Patent No.: US 10,744,200 B2
(45) Date of Patent: Aug. 18, 2020

(54) METHOD FOR PREPARATION OF ALUMINIUM PHOSPHATE GEL FOR APPLICATION IN VACCINE FORMULATIONS

(71) Applicant: BIOLOGICAL E LIMITED, Hyderabad, Telangana (IN)

(72) Inventors: Ravi Ganapathy, Hyderabad (IN); Nagireddy Gade, Hyderabad (IN); Manish Manohar, Hyderabad (IN); Vikram Madhusadan Paradkar, Hyderabad (IN); Mahima Datla, Hyderabad (IN)

(73) Assignee: BIOLOGICAL E LIMITED (IN)

( * ) Notice: Subject to any disclaimer, the term of this patent is extended or adjusted under 35 U.S.C. 154(b) by 104 days.

(21) Appl. No.: 15/772,777

(22) PCT Filed: Jun. 13, 2016

(86) PCT No.: PCT/IN2016/000151
§ 371 (c)(1),
(2) Date: May 1, 2018

(87) PCT Pub. No.: WO2016/199162
PCT Pub. Date: Dec. 15, 2016

(65) Prior Publication Data
US 2019/0240322 A1 Aug. 8, 2019

(30) Foreign Application Priority Data
Jun. 12, 2015 (IN) .......................... 2963/CHE/2015

(51) Int. Cl.
*A61K 39/39* (2006.01)
*C01B 25/36* (2006.01)
*A61K 9/06* (2006.01)
*A61K 39/00* (2006.01)

(52) U.S. Cl.
CPC ................ *A61K 39/39* (2013.01); *A61K 9/06* (2013.01); *C01B 25/36* (2013.01); *A61K 2039/55505* (2013.01); *C01P 2004/51* (2013.01); *C01P 2004/60* (2013.01); *C01P 2004/61* (2013.01)

(58) Field of Classification Search
CPC ............. C01P 2004/51; C01P 2004/60; C01P 2004/61; A61K 39/39; A61K 9/06; A61K 2039/55505; C01B 25/36
See application file for complete search history.

(56) References Cited

U.S. PATENT DOCUMENTS

| 3,271,299 A * | 9/1966 | Kearby .................. C10G 45/06 208/114 |
| 8,540,955 B2 * | 9/2013 | Khandke ................ A61K 33/06 423/304 |
| 2013/0198880 A1 * | 8/2013 | Babb .................. A01K 67/0278 800/18 |

FOREIGN PATENT DOCUMENTS

| DE | 2152228 | 4/1973 |
| RU | 2149138 | 5/2000 |
| SU | 481539 | 8/1975 |
| SU | 559895 | 5/1977 |
| SU | 550340 | 3/1997 |
| WO | WO 2009/136233 | 11/2009 |
| WO | WO 2013/078102 | 5/2013 |

OTHER PUBLICATIONS

Burrell et al. (Aluminum phosphate adjuvants prepared by precipitation at constant. Part II: physiochemical properties, 2001, Vaccine, vol. 19, pp. 282-287. (Year: 2001).*

Burrell et al., "Aluminium phosphate adjuvants prepared by precipitation at constant pH. Part I: composition and structure," Vaccine 19(2-3):275-81 (publication date: Sep. 15, 2000).

Burrell et al., "Stability of aluminium-containing adjuvants to autoclaving," Vaccine 17(20-21):2599-2603 (publication date: Jun. 4, 1999).

Glenny et al., "Immunological Notes, XVII-XXIV," The Journal of Pathology and Bacteriology 29:31-40 (1926).

International Search Report and Written Opinion dated Nov. 29, 2016 for International Application No. PCT/IN2016/000151.

Scholtz et al., "Desorption of Carbonate from Aluminum Hydroxycarbonate Gel by Nitrogen Purging," Journal of Pharmaceutical Sciences 73(2):209-12 (publication date: Feb. 1984).

Scholtz et al., "Exchange of Sodium by Magnesium in Aluminum Hydroxycarbonate Gel," Journal of Pharmaceutical Sciences 73(7):1007-9 (publication date: Jul. 1984).

* cited by examiner

*Primary Examiner* — Ali Soroush
(74) *Attorney, Agent, or Firm* — Perkins Coie LLP

(57) ABSTRACT

The present invention relates to an improved process for production of Aluminium phosphate (AlPhos) gel wherein the solutions of aluminium salt and alkaline phosphate salt are added to water by maintaining the pH under stirring to obtain the precipitate, followed by sterilization of the said precipitate and finally obtaining the Aluminum phosphate gel.

11 Claims, No Drawings

METHOD FOR PREPARATION OF ALUMINIUM PHOSPHATE GEL FOR APPLICATION IN VACCINE FORMULATIONS

FIELD OF THE INVENTION

The present invention relates to an improved process for production of Aluminium phosphate (AlPhos) gel. It also relates to the use of Aluminium phosphate gel, especially in immunogenic/and or vaccine compositions, for adsorption of antigen(s).

BACKGROUND OF THE INVENTION

Vaccine composition may comprise one or more of adjuvants. 'Adjuvants' are substances that are incorporated into, or injected simultaneously, with an antigen and that potentiate non-specifically the ensuing immune responses. The resultant immune responses last longer by maintenance of sufficient levels of antibodies in the administered population. For practical and economic reasons, this prophylactic immunization needs to be obtained with minimum number of administrations and employing least amount of antigen compatible with efficient immunization. The nature of these adjuvants may be inorganic like alum, such as aluminium phosphate and aluminium hydroxide which are most commonly used in human vaccines, and organic adjuvants like squalene.

Veterinary vaccines commonly make use of oil-based adjuvants. A vaccine used for prevention of influenza caused by H5N1 virus, which is commonly referred to as an avian influenza or "bird flu", contains the adjuvant AS03, an oil-in-water emulsion. The AS03 adjuvant is made up of the oily compounds D, L-alpha-tocopherol (vitamin E), squalene, an emulsifier—polysorbate-80, which helps ingredients to mix together and keep them from separating, and water containing small amounts of salts.

Aluminium salts are widely used, since 1930s. The only adjuvants approved by the Food and Drug Administration for use in human vaccines are aluminium-containing adjuvants, due their long history of safe and effective use. Glenny et al., had described the effect of aluminium compounds as adjuvant (Glenny A T, Pope C G Waddington H, Wallace U. Immunological Notes XVII to XXIV. J. Pathol. 29, 31-40, 1926).

Despite this, aluminium-containing adjuvants have been described as being difficult to manufacture with reproducible physicochemical properties. Scholtz et al., in 1984, prepared pure aluminium phosphate using equimolar amounts of aluminium chloride and trisodium phosphate.

Aluminium Phosphate gel is used as the 'adjuvant' in the formulations of the liquid pentavalent vaccine (LPV), helping to boost the immunogenic responses to Hepatitis-B Surface Antigen, Diphtheria and Tetanus toxoids which get adsorbed onto the gel particles, and also possibly for the whole-cell Pertussis antigens. The aluminium salts are used in. DTaP vaccines, the pneumococcal conjugate vaccine and hepatitis-B vaccines. Although there has been a search for alternate adjuvants, aluminium compounds (aluminium phosphate and hydroxide) will continue to be used as adjuvants for human vaccines for many years owing to their good track record of safety, low cost and adjuvanticity with a variety of antigens.

Two methods have been commonly used to prepare vaccines and toxoids with aluminium compounds—in situ precipitation of aluminium compounds in the presence of antigen (developed originally to purify toxoids by precipitation with alum), and adsorption of antigen onto preformed aluminium gel. Adsorption of antigens on aluminium adjuvants, either during in situ precipitation of aluminium adjuvants or onto preformed aluminium gels, depends upon physical and chemical characteristics of antigen, type of aluminium adjuvant and conditions of adsorption. These conditions are often overlooked, and a poorly formulated aluminium adjuvant preparation does not exhibit optimal adjuvanticity.

SU481539 disclosed a method of producing a porous hydrogel alumino-phosphate by reacting aluminium chloride with 85% phosphoric acid. The resulting solution was cooled to −8 to −10° C., slowly introduced with vigorous stirring, cooled to the same temperature as ethylene oxide. The resulting gel was heated at a temperature of 50-350° C. and a water vapour pressure of 1-170 atm for 2 hours, washed with distilled water, dried and calcined at 200° C. in air at 650-700° C. for 4-6 hours.

SU550340 disclosed a method of producing aluminium phosphate gel by reacting aluminium acetate with phosphoric acid, followed by filtration, washing, drying at 30-40° C. for 12 hours, then at 110-120° C. for 4 hours and at 600° C. product activation within 4 hours. The proposed method is also complicated and laborious, because it requires prolonged drying time and the activation of the final product at high temperatures.

SU559895 disclosed a method of producing an amorphous aluminium phosphate hydrate by reacting a solution of aluminium nitrate and phosphoric acid in the molar ratio 1:0.95-1.05, followed by neutralization with ammonia to pH=6.0 with temperature in the range of 15-20° C. The resulting product is filtered, washed with water and dried at a temperature of 60-80° C.

DE 2152228 disclosed a process, for the production of aluminium phosphate gel, which comprises of forming a mixture of sodium aluminate, phosphoric acid and aluminium sulphate in aqueous medium, reacting the mixture in such a way that the pH value of the resulting suspension is between 5 and 6, and heating the aluminium phosphate, which is precipitated, to a temperature above 70° C. either during or after its precipitation.

RU2149138C disclosed a process of producing Aluminium phosphate gel wherein an initial solution of water-soluble salts of aluminium and sodium phosphate was subjected to filtration on microfiltration unit with a threshold bandwidth of 0.22 microns, and reacted with a soluble aluminium salt with sodium phosphate. The desired product was precipitated under vigorous stirring for 15-45 min. at a rotation speed of the stirrer of 3.3-8.3 sec$^{-1}$. Aluminium phosphate gel is formed at a temperature of 18-60° C. for 5-7 days, followed by its washing.

WO 2009/136233A1 disclosed method for production of nanoparticles of aluminium phosphate with particle diameter less than 1000 nm, preferably 10 to 600 nm, comprising: a. preparation of aluminium phosphate gel; b. adjusting pH of the aluminium phosphate gel; c. subjecting the aluminium phosphate gel to size reduction; d. affording aluminium phosphate nanoparticles of desired size; and e. optionally suspending the nanoparticles in a suitable buffer, wherein the aluminium phosphate gel can be prepared (i) in situ, (ii) by suspending aluminium phosphate powder in suitable solvent, or (iii) by treatment of equimolar aluminium chloride with trisodium phosphate to effect aluminium phosphate gel formation, followed by chloride removal, if required.

U.S. Pat. No. 8,540,955 disclosed an improved method, for producing the aluminium adjuvant AlPO$_4$, which comprises the steps of mixing a solution of aluminium chloride and a solution of sodium phosphate tribasic to produce an aluminium phosphate precipitate, wherein the improvement comprises settling the aluminium phosphate precipitate at a temperature in the range of about 50° C. to about 70° C.

Burrell et al. [Vaccine. 1999 Jun. 4;17(20-21):2599-603] disclosed that Aluminium phosphate adjuvant remained amorphous when autoclaved for 30 or 60 min. at 121° C. However, deprotonation and dehydration reactions occurred as evidenced by a decrease in the pH. The protein adsorption capacity, rate of acid neutralization at pH 2.5 and point-of-zero charge also decreased, indicating that the deprotonation/dehydration reactions resulted in a decreased surface area.

Buttell et al. [Vaccine. 2000 Sep. 15;19(2-3):275-81] disclosed a process for preparing Aluminium phosphate adjuvant wherein an aqueous solution containing aluminium chloride and sodium dihydrogen phosphate was pumped into the reaction vessel at a constant rate. A second pump infused a sodium hydroxide solution at the rate required to maintain the desired pH. Precipitations were performed between pH 3.0 and 7.5, at intervals of pH 0.

The characteristics of aluminium adjuvants, such as size of the gel particles, adsorption capacity, isoelectric point, and ratio of aluminium to phosphate depend upon the conditions of making these gels, including order of adding reagents, speed at which the reagents are added & mixed, mixing speed, time taken to adjust pH, and scale of gel preparation. Therefore, aluminium adjuvants have been described as difficult to manufacture in a physico-chemically reproducible way, thus resulting in batch to batch variations.

The methods of preparing aluminium phosphate gel disclosed in the above prior arts are tedious and complex. Although methods for producing aluminium phosphate adjuvant have been described, there remains a need in the art for methods that are more efficient on an industrial scale. In addition, it is desirable that the characteristics of aluminium phosphate adjuvant produced by any new method should satisfy the properties of the adjuvant already present in various marketed products to enable its usage in vaccine preparations.

Objective of the Invention

The main objective of the present invention is to provide an improved process for the production of Aluminium phosphate gel through a simple and cost-effective method.

An another objective of the present invention is to avoid use of addition of alkali or acid for different pH management as previously used in the state of art, rather the process materials and parameters are adjusted so that the Aluminium phosphate gel is produced in optimised conditions and concentration; this would avoid use of alkalis like carbonates and hydroxides that would create new species of salts and non-uniform gel structure which, therefore, may require removal.

Yet another objective of the present invention is to have a method which is simple, easy to control, quicker to produce and which avoids extreme temperatures or long durations for maturation, etc.

A final objective of the present invention is to demonstrate suitability of the aluminium phosphate gel prepared as described in vaccine preparations as an adjuvant.

In a nut-shell, the invention relates an improved, scalable process for producing a sterile Aluminium Phosphate Gel with good efficiency, but reduced time, efforts and cost, with demonstration of its suitability in making stable vaccine preparations.

SUMMARY OF THE INVENTION

The present invention provides an improved process for the preparation of Aluminium Phosphate Gel which comprises of:
i) adding the solutions of aluminium salt and alkaline phosphate salt to water, by maintaining the pH between 3.0 and 4.0, under stirring to, obtain a precipitate;
ii) sterilizing the aluminium phosphate precipitate of step (i), by heating the aluminium phosphate precipitate to a temperature in the range of 120-150 ° C. for a period of 30 to 90 minutes; and
iii) obtaining the aluminium phosphate gel having particles with a size distribution having d(50) in the range of 3.0 µm to 9.0 µm and a mean particle size less than 7 µm, wherein the process is devoid of the steps of settling the aluminium phosphate suspension and removal of supernatant.

Essentially the invention relates to the process for producing Aluminium Phosphate Gel with controlled and consistent particle size distribution, by manipulation of solutions' concentrations, mixing parameters and addition rates, but without any need for sizing and gel-washing steps.

DETAILED DESCRIPTION OF THE INVENTION

The present invention provides a method of producing aluminium phosphate gel which comprises the steps of adding aluminium salt and alkaline phosphate salt to water by maintaining the pH between 3.0 and 4.0, under stirring to obtain a precipitate.

Aluminium salt, as used according to the present invention, is in the form of Aluminium chloride hexahydrate.

Alkaline phosphate used according to the present invention is Sodium phosphate, preferably, tribasic sodium phosphate or dibasic sodium phosphate.

The pH is maintained by adding specific concentrations of the solutions of aluminium chloride and trisodium phosphate. Preferably, the concentration between 400 and 500 milliMolar (mM) is used, more preferably between 480 and 490 mM is used.

Both aluminium chloride and trisodium phosphate are added to water under stirring for a period of 10 to 60 minutes, preferably, 35 to 55 minutes, with the addition of initial amount of aluminium chloride solution for a period of 1 to 60 seconds, preferably 30 seconds, more preferably 2 to 10 seconds, prior to the addition of sodium phosphate solution, so as to maintain the pH of precipitation between 3.0 and 4.0, preferably between 3.2 and 3.5, almost throughout the reaction except the last 5-10% part of addition.

The solutions are added to water under stirring at not less than 400 rpm, preferably between 500 and 600 rpm, and more suitably at the mid-to higher range.

The solutions of aluminium chloride and trisodium phosphate are added to water at room temperature or at a temperature between 20° C. and 25° C.

The solutions of aluminium chloride and trisodium phosphate are added and mixed with water in a vessel, which has baffles, minimum 2 and preferably between 2 and 4 in number. The stirring mechanism is top-mounted and the stirring rod has at least 3 impellers, each having not less than 4 blades.

According to the process of the present invention, gel is formed at a pH range of 3.2 to 3.5 without addition of any other acid or alkali. This method may be used to provide a gel with a concentration not more than 3 mg/mL of aluminium, preferably, in the range up to 2.5 mg/mL of 'aluminium'.

The Aluminium phosphate gel prepared according to the present invention has a particle-size distribution wherein d(90) is in the range of <15 μm, preferably 5 to 10 μm.

The efficiency of the method is improved significantly by adding the aluminium chloride and sodium phosphate tribasic to water at a constant ratio, and by maintaining pH & temperature. Such a process also makes the steps required in purification and concentration of final product, i.e. Aluminium Phosphate Gel, redundant.

In yet another embodiment, the process involves, sterilizing the aluminium phosphate precipitate of step (i) by heating the aluminium phosphate precipitate to a temperature in excess of 120° C., preferably, 120-150° C. for a period of not less than 30 minutes, and preferably 30 to 90 minutes.

Another improvement of the present invention is performing the process steps within a closed system, thereby increasing the sterility assurance of the final product and reducing the need for sterility testing. This makes the overall process more efficient since it reduces the number of sterility tests that need to be performed.

In yet another embodiment, the present invention provides a process for the preparation of sterile Aluminium Phosphate gel aseptically within 60 minutes, more preferably within 45 minutes with the use of pre-sterilized WFI in a vessel, sterile-filtered chemical solutions and other process-related accessories, which can be immediately used for formulation of vaccines without any purification, sizing or other testing.

In yet another embodiment, the Aluminium Phosphate gel produced according to present invention is more resistant to changes in particle sizing and other physicochemical parameters. Further, the pH of the gel, post-sterilization, is in the range more suitable for blending of antigens which have an iso-electric point (pI) above 5.0, and thereby requiring no pH adjustment.

In yet another embodiment, the present invention provides a process for the preparation of sterile Aluminium Phosphate gel which, unexpectedly, aids in avoiding the steps of settling and thereby there is no formation of supernatant. Hence, the entire process is completed within a time period of 1 to 5 hours, towards the latter if a post-preparation sterilization mode is followed, which makes it simple, economical and operationally highly feasible.

In a preferred embodiment, the present invention provides a process for the preparation of Aluminium Phosphate Gel which comprises the steps of:
i) adding the solutions of aluminium chloride and trisodium phosphate to water for injection under stirring within 60 minutes, preferably between 35 to 55 minutes, by maintaining the pH of the precipitate formed between 3.0 and 4.0, preferably between 3.2 and 3.5;
ii) sterilizing the aluminium phosphate precipitate of step (i) by heating the aluminium phosphate precipitate to a temperature in the range of 120-150° C. for a period of 30 to 90 minutes; and
iii) obtaining the aluminium phosphate gel having particles with a size distribution having d(50) in the range of 3.0 μm to 9.0 μm and a mean particle size less than 7 μm, wherein the process is devoid of the steps of settling the aluminium phosphate suspension and removal of supernatant.

The Aluminium Phosphate adjuvant prepared according to the present invention remained stable during the shelf life when stored at or below room temperature.

In a more preferred embodiment, the present invention provides a method of producing aluminium phosphate gel having a particle size distribution wherein d(90) is in the range of <15 μm, which comprises the steps of:
i) adding the solutions of aluminium chloride and trisodium phosphate at a concentration between 400 and 500 milliMolar (mM) to Water For Injection, wherein initial amount of aluminium chloride solution is added 2 to 10 seconds, prior to the addition of sodium phosphate solution, under stirring within 60 minutes, preferably between 35 to 55 minutes, by maintaining the pH of the precipitate formed between 3.0 and 4.0, preferably between 3.2 and 3.5;
ii) sterilizing the aluminium phosphate precipitate of step (i) by heating the aluminium phosphate precipitate to a temperature in the range of 120-150° C. for a period of 30 to 90 minutes and,
iii) obtaining the aluminium phosphate gel having particles with a size distribution having d(50) in the range of 3.0 μm to 9.0 μm and a mean particle size less than 7 μm, wherein the process is devoid of the steps of settling the aluminium phosphate suspension and removal of supernatant.

The mechanism of adjuvanticity of aluminium compounds includes formation of a depot, efficient uptake of aluminium adsorbed antigen particles by antigen presenting cells due to their particulate nature and optimal size (<10 μm); and stimulation of immune competent cells of the body through activation of complement.

In yet another embodiment, the present invention provides a formulation process of vaccine which comprises the steps of:
i. adding the solutions of sterile-filtered aluminium chloride and trisodium phosphate to pre-sterilized water for injection under stirring within 60 minutes, preferably between 35 to 55 minutes, by maintaining the pH of the precipitate formed between 3.0 and 4.0, preferably between 3.2 and 3.5;
ii. adding the antigens to the aluminium phosphate gel obtained in step (i) immediately without any purification, sterilization, sizing.

In yet another embodiment, the present invention provides use of Aluminium Phosphate Gel prepared according to the process for adsorption of antigens in vaccine preparations.

Advantages of the Invention

1. The process of the present invention does not involve any addition of acid/alkali for pH adjustment.
2. The process does not involve any step for particle size reduction of aluminium phosphate gel.
3. The process does not involve the steps of settling and thereby removal of supernatant.
4. The process does not involve any washing step.
5. The process avoids high temperature conditions and longer durations for maturation.

The present invention will be more specifically illustrated with reference to the following examples. However, it should be understood that the present invention is not limited by these examples in any manner, but includes variations thereof within the parameters described herein, as can be known to those well-versed in the art.

Example-1. Preparation of Aluminium Phosphate Gel.

Solutions of aluminium chloride and trisodium phosphate at a concentration of 485±1 mM were used as raw materials and Water For Injection (WFI) as the solvent for producing the aluminium phosphate gel. Both solutions were added as shown in the Table given below at a constant rate, within 45±10 minutes, to WFI (at a volume 3.1-3.15X of a solution's volume) under stirring at 550±50 rpm in a vessel having 2-4 baffles, a top-mounted stirrer with minimum 3 impellers at different heights and each having 4-blades. Addition of aluminium chloride solution was started 2-5 seconds prior to start of addition of Sodium phosphate solution to maintain the pH of precipitation below 3.5 throughout the process, except for the last 5-10% of addition time, during which the pH was seen to rise to around 5.0. Post-completion of addition, the gel was sterilized in situ using steam at ≥121.1° C. for 30-45 minutes. pH of the gel, post-sterilization, reduced by ~1 unit to reach around 4.0±0.3.

TABLE 1

Aluminium Phosphate Gel Preparation

| Stock Solutions | Qty./L | Solution volumes required for gel volume of . . . | | |
|---|---|---|---|---|
| | | 1.8 L | 18 L | 40 L |
| Aluminium Chloride (Solution 1) | 117.1 g/L | 350 ml | 3.5 L | 7.7 L |
| Tri-Sodium Phosphate (Solution 2) | 184.3 g/L | 350 ml | 3.5 L | 7.7 L |
| WFI required | | 1.1 L | 11 L | 24.6 L |

Final Concentration of both salts in the gel is 94.3 mM; 1:1 ratio.

Aluminium phosphate gel, using the above process, was produced from 1L to 40L scales, giving results reproducibly at each scale provided the parameters are within the given range. There is no other settling, purification—i.e. washing of the gel using any buffers for e.g. saline, etc. in this process and hence it is very simple, straight-forward and results in a gel which is ready-to-use for blending. The process, thereby, proved its versatility, scalability and its cost-effectiveness, thereby confirming its suitability for commercial production.

Example-2. Particle size of Aluminium Phosphate Gel Preparation.

The particle size of the aluminium phosphate gel prepared as described in Example 1 was determined and the mean particle size was found to be in the range of not more than 7 μm, with the d(10), d(50) & d(90) ranges being >1 μm, 3-8 μm and <14μm, respectively, without any additional processing step, e.g. homogenization, fines selection/removal, etc. Representative data for pH and particle sizes, along with PZC and Zeta-potential values, estimated during preparation of gel lots made at 18L and 40L scales, both before and after sterilization, is given in Table-2. The data indicates that without any of the additional process requirements, the process has proven its simplicity and reproducibility.

TABLE 2 pH, Particle Size Ranges & Other Parameters Tested on 3 Lots Each of Aluminium Phosphate Gel (AlPhos Gel) prepared at 18 L and 40 L Scales

| | | Batch No. | | | | | | | | | | | |
|---|---|---|---|---|---|---|---|---|---|---|---|---|---|
| | | 18 L | | | | | | 40 L | | | | | |
| | | APG 18/01 | | APG 18/02 | | APG 18/03 | | APG 40/01 | | APG 40/02 | | APG 40/03 | |
| | | BS | AS | BS | AS | BS | AS | BS | AS | BS | AS | BS | AS |
| pH | | 5.2 | 4.31 | 5.23 | 4.1 | 4.88 | 3.91 | 4.9 | 4.06 | 5.1 | 4.2 | 4.9 | 3.82 |
| Particle Size (μm) | Mean | 3.64 | 4.75 | 3.59 | 5.64 | 3.68 | 4.18 | 4.26 | 4.85 | 3.42 | 4.63 | 3.64 | 4.33 |
| | $d_{10}$ | 2.07 | 3.15 | 2.07 | 2.68 | 2.01 | 2.71 | 2.73 | 3.26 | 2.03 | 3.19 | 2.28 | 2.66 |
| | $d_{50}$ | 4.77 | 6.7 | 4.51 | 7.84 | 4.35 | 5.62 | 4.74 | 6.13 | 3.92 | 6.54 | 4.07 | 5.28 |
| | $d_{90}$ | 8.26 | 10.9 | 7.7 | 12.7 | 8.89 | 9.88 | 7.33 | 10.0 | 6.75 | 10.2 | 6.54 | 8.83 |
| PZC | | 5.19 | 5.4 | 5.23 | 5.39 | 5.48 | 5.44 | 5.1 | 5.18 | 5.27 | 5.35 | 5.27 | 5.34 |
| Zeta Potential @ pH 7.5 | | −31.1 | −35.7 | −31.8 | −32.0 | −26.5 | −28.8 | −33.5 | −35.0 | −31.9 | −32.4 | −30.8 | −32.3 |

BS = Before Sterilization;
AS = After Sterilization.

Example-3. Formulation of Aluminium Phosphate Gel Adjuvant in Immunogenic Compositions.

The aluminium phosphate gel prepared as described in the Example-1, was used in formulation of liquid pentavalent vaccine (LPV) comprising Diphtheria toxoid (DT), Tetanus Toxoid (TT), Whole-cell pertussis (wP), Hepatitis-B surface antigen (HBsAg) and Haemophilus influenzae type-b Polyribosyl Ribitol phosphate-TT conjugate (Hib) as the antigenic components, in saline as the final diluent. In this formulation, to the gel obtained as in Example-1 under stirring at 200-300 rpm the HBsAg, DT and TT antigens were added one after the other without requirement of any pH adjustment, as it is the ideal pH for their adsorption to the gel (adjuvant) as per literature and proved in our studies. This blend was then added with up to 80% of saline required for final volume make-up followed by addition of wP; then the whole blend was chilled to below 10° C., and Hib component was added with stirring. The final volume was then made-up to the required level with saline. The pH of the blend, if required, was then adjusted to be between 6.2 and 6.5, but was not found to be necessary in most cases.

The process, as described above, was optimized for the LPV blending process using the aluminium phosphate gel prepared as described in Example 1 at different scales. LPV blends of volumes ranging from 100 mL to 60L was made using this process, and all were tested and proved to meet the specifications for the vaccine, including the safety and potency parameters of each antigen used in the formulation.

The aluminium phosphate gel was also shown to be suitable in the preparation of Liquid Quadravalent vaccine (LQV) comprising Diphtheria toxoid (DT), Tetanus Toxoid (TT), Whole-cell pertussis (wP), and Haemophilus influenzae type-b Polyribosyl Ribitol phosphate-TT conjugate (Hib) as the antigenic components, in saline as the final diluent. The formulation of this vaccine follows the same antigens and sequences of their addition, except non-use of HBsAg which is added first in the LPV preparation.

LQV blends of volumes ranging from 1L to 60L have been made using this process, and all have been tested and proved to meet the specifications for the vaccine, including the safety and potency parameters of each antigen used in the formulation.

Example-4. Antigen Adsorption Capacity Procedure and Results.

Among the antigens used for formulating LPV HBsAg, DT & TT were the three which bind to aluminium phosphate gel. The in-house requirement for binding in LPV for HBsAg was ≥90%, for that of DT it was ≥28% and for TT it was ≥30%. The aluminium phosphate gel produced at different scales has consistently met these requirements, when tested as produced up to 40L gel lot and LPV blend volume of up to 60L. The variations in the % adsorption values between LPV blends produced using the Aluminium Phosphate gel prepared as per the procedure described in Example-1, both made at different scales, is insignificant. Also, exposure of the vaccine to stress conditions (37° C. for 14 days) did not change the % adsorption values significantly. A representative example of this property of the gel, made at different scales (1L and 18L) and used for LPV blending at 2L and 60L scales, along with a 2L and 60L blends of LPV made using Adju-Phos® of Brenntag Biosector (commercial supplier) is summarised in Table-3.

As an example of the proof of stability of the gel/LPV blend made using the Aluminium Phosphate gel prepared as per Example-1, the % adsorption results for the three antigens of a 4L LPV blend made and tested on days 0 (release), after incubation at 37° C. on days 5, 7 & 14 are summarised in Table-4.

TABLE 3

% Adsorption Results, in LPV Blends with Different Gel Sources & Blend Sizes

| S. No. | Antigen | Adju-Phos ® (Brenntag) | | Prepared as per the procedure described in Example-1 | |
|---|---|---|---|---|---|
| | | 2 L LPV | 60 L LPV | 2 L LPV | 60 L LPV |
| 1 | HBsAg | 94.8 | 99.7 | 98.8 | 98.9 |
| 2 | Diphtheria Toxoid | 47.6 | 59.6 | 50.0 | 58.3 |
| 3 | Tetanus Toxoid | 41.7 | 46.7 | 44.8 | 46.7 |

The data presented in Table-3 confirm that the % adsorption of the aluminium phosphate gel prepared as per the procedure described in Example-1 matches with that of Adju-Phos of Brenntag.

TABLE 4

% Adsorption Results - 4 L LPV Blend at Release (Day-0) & After Incubation at 37° C. for 14 days

| Sampling Day | Diphtheria | Tetanus | HBsAg |
|---|---|---|---|
| Day-0 | 50.0 | 40.72 | 96.5 |
| Day-5 | 77.1 | 53.8 | 98.7 |
| Day-7 | 41.7 | 48.6 | 99.2 |
| Day-14 | 56.8 | 47.5 | 98.9 |

Example-5. Other Procedures for Characterizing the Gel and Their Results.

Several lots of aluminium phosphate gel produced as described in Example 1 were analysed for various physico-chemical properties so that they are fully characterized. Other than pH, particle size and aluminium content, few more parameters were also tested which, along with the reasons for their analysis, are summarised in Table-5.

TABLE 5

Physico-chemical Properties of AlPhos Gel to be Tested & Rationale

| Parameter | Limit | Impact/Reason for Analysis |
|---|---|---|
| Appearance | White turbid suspension in which the mineral carrier tends to settle down slowly upon | Describes the general physical appearance |
| Aluminium content | Not Less Than 2 mg/mL | Determines the binding capacity |
| Particle size (μm) Mean $D_{10}$ $D_{50}$ $D_{90}$ | Nor More Than (NMT) 7 ≥1 3-8 ≤14 | Determines surface area, aggregation potential, binding capacity |
| PZC (pI) | 5.1 ± 0.5 | |
| Zeta Potential (@ pH 7.5) | −28 to −40 mV | Determines adsorption ratio/rates; main factor determining aggregation; also determines the stability of suspension |
| Antigen Adsorption capacity | rHBsAg: ≥90% DT: ≥28% TT:: ≥30% | Determines relative distribution of antigens in sol/gel phases |
| Impurity Profile Free aluminium | NMT 50 ppm | Gives indication of gel purity |
| Soluble Phosphates | NMT 0.5% as $PO_4$ | |
| Specific Gravity/ Sedimentation Rate | 1.00-1.03 NMT 35% | Determines weight/unit Determines the settleability of the gel |
| Osmolality | 550 ± 50 mOsm/Kg | Reflects the concentration of solutes in the gel |

Representative quantitative data from the six batches of Aluminium Phosphate Gel produced at 18L scale prepared as per the procedure described in Example-1 for process validation batches of LPV and LQV batches are summarised in Tables 6 & 7. All these batches complied with requirements for all the parameters tested at both post- & pre-sterilization stages; while all batches complied with the specifications for appearance, sterility and impurities levels, the quantitative parameters among those were analysed in these tables.

TABLE 6

Analysis of Results of Physico-chemical Parameters Testing of
Aluminium Phosphate Gel Prepared as per the procedure described in
Example-1 - Pre-Sterilization Stage

| S. No. | Test | | In LPV Batches | | | In LQV Batches | | | Analyses | | |
|---|---|---|---|---|---|---|---|---|---|---|---|
| | | | LPV-1 | LPV-2 | LPV-3 | LQV A | LQV-B | LQV-C | Avg. | Std. Dev. | % CV |
| 1 | Particle size ($\mu$m) | Mean | 3.50 | 3.19 | 3.24 | 3.50 | 3.62 | 3.73 | 3.46 | 0.21 | 6.10 |
| | | $D_{10}$ | 2.03 | 1.86 | 1.93 | 1.97 | 2.12 | 2.26 | 2.03 | 0.14 | 7.09 |
| | | $D_{50}$ | 4.2 | 3.67 | 3.68 | 4.4 | 4.19 | 4.29 | 4.07 | 0.32 | 7.77 |
| | | $D_{90}$ | 7.34 | 6.43 | 6.28 | 7.82 | 7.26 | 7.19 | 7.05 | 0.59 | 8.31 |
| 2 | PZC (pI) | | 5.33 | 5.44 | 5.41 | 5.49 | 5.50 | 5.36 | 5.38 | 5.43 | 0.06 |
| | | | -32.8 | -32.6 | -31.8 | -33.4 | -30.7 | -33.7 | -32.3 | -32.3 | 1.5 |
| 3 | Zeta Potential (@ pH 7.5) | | -32.8 | -32.6 | -31.8 | -33.4 | -30.7 | -33.7 | -32.3 | -32.3 | 1.5 |
| 4 | Sedimentation Rate @ 48 hours (in %) | | 27 | 25 | 25 | 25 | 25 | 25 | 25 | 25.0 | 0.0 |

The CV (Co-efficient of Variation) values for all parameters tested, without considering the individual distribution ranges of particle sizes, were well within 10% and more so with the post-sterilization stage; this indicated good consistency of the gel preparation procedure over six batches analysed, produced over a period of 6 months with different lots of input materials. The data also confirmed that only minor, insignificant changes occur post-sterilization in physico-chemical parameters of the gel.

Some of these parameters, for a few batches, have been tested over the gel's storage period (up to 7 days) at different stages viz. after preparation, after in-situ sterilization, and after autoclaving of in-situ sterilized gel. Representative data from one batch tested for storage effect on different parameters is summarized in Table-8. The data confirm that the parameters do not change much up to 7 days post-sterilization/autoclaving. These characterization data and their analyses confirm the consistency of the gels made at different scales and also reconfirm the robustness of the gel preparation process.

TABLE 7

Analysis of Results of Physico-chemical Parameters Testing of Aluminium
Phosphate Gel Prepared as per the procedure described in Example-1 -
Post-Sterilization Stage

| S. No. | Test | | In LPV Batches | | | In LQV Batches | | | Analyses | | |
|---|---|---|---|---|---|---|---|---|---|---|---|
| | | | LPV-1 | LPV-2 | LPV-3 | LQV A | LQV-B | LQV-C | Avg. | Std. Dev. | % CV |
| 1 | Aluminium content | | 2.42 | 2.42 | 2.395 | 2.05 | 2.15 | 2.10 | 2.26 | 0.17 | 7.71 |
| 2 | pH | | 3.77 | 4.28 | 4.31 | 3.91 | 4.04 | 4.21 | 4.09 | 0.22 | 5.32 |
| 3 | Particle size ($\mu$m) | Mean | 4.13 | 3.91 | 4.00 | 4.24 | 3.90 | 4.00 | 4.03 | 0.13 | 3.28 |
| | | $D_{10}$ | 2.49 | 2.57 | 2.39 | 2.52 | 2.46 | 2.38 | 2.47 | 0.07 | 3.00 |
| | | $D_{50}$ | 5.48 | 4.07 | 4.97 | 5.73 | 5.15 | 4.68 | 5.01 | 0.59 | 11.81 |
| | | $D_{90}$ | 9.29 | 7.63 | 8.45 | 9.63 | 8.51 | 7.85 | 8.56 | 0.78 | 9.14 |
| 4 | PZC (pI) | | 5.33 | 5.48 | 5.54 | 5.47 | 5.44 | 5.4 | 5.44 | 0.07 | 1.33 |
| 5 | Zeta Potential (@ pH 7.5) | | -32.8 | -31.27 | -33.43 | -33.9 | -33.03 | -34.17 | -33.7 | 0.60 | 1.77 |
| 6 | Specific Gravity | | 1.020 | 1.020 | 1.019 | Not Checked | | | Not Applicable | | |
| 7 | Osmolality | | 528 | 542 | 509 | Not Checked | | | Not Applicable | | |
| 8 | Sedimentation Rate @ 48 hours (in %) | | 27 | 28 | 28 | 28 | 27 | 28 | 27.7 | 0.52 | 1.87 |

TABLE 8

Physico-Chemical Parameters of an Aluminium Phosphate
Gel Batch at Different Stages of Production and Storage

| Stage | Particle Size ($\mu$m) | | | | pH | PZC | ZP (@ pH 7.5) | Osmolality (mOsm/Kg) | Sedimentation Rate (%), @ 48 hrs. |
|---|---|---|---|---|---|---|---|---|---|
| | $D_{10}$ | $D_{50}$ | $D_{90}$ | Mean | | | | | |
| After Preparation | 2.21 | 4.73 | 8.38 | 3.79 | 5.51 | 5.2 | -32.87 | 518 | 25 |
| Post in situ sterilization | 2.90 | 5.60 | 9.30 | 4.44 | 4.20 | 5.0 | -31.93 | | 28 |

TABLE 8-continued

Physico-Chemical Parameters of an Aluminium Phosphate
Gel Batch at Different Stages of Production and Storage

| Stage | | Particle Size (μm) | | | | pH | PZC | ZP (@ pH 7.5) | Osmolality (mOsm/Kg) | Sedimentation Rate (%), @ 48 hrs. |
|---|---|---|---|---|---|---|---|---|---|---|
| | | $D_{10}$ | $D_{50}$ | $D_{90}$ | Mean | | | | | |
| Post autoclaving of in-situ sterilized gel (Day-0) | | 2.99 | 5.79 | 9.73 | 4.52 | 4.20 | 5.0 | −32.10 | Not Checked | 28 |
| Post autoclaving of in-situ sterilized gel (Day-7) | | 2.94 | 5.79 | 10.04 | 4.54 | 4.65 | 5.0 | −34.67 | | 28 |
| Post-autoclaving only | Day-0 | 2.19 | 4.74 | 8.45 | 3.78 | 4.30 | 5.1 | −32.00 | 523 | 26 |
| | Day-7 | 2.33 | 4.92 | 9.19 | 3.94 | 4.68 | 5.2 | −33.27 | 524 | 25 |

Example-6. Efficacy & Stability of AlPhos gel as Adjuvant in Vaccine Preparations.

Three batches of 60L LPV were formulated with three different batches of aluminium phosphate gel prepared as described in Example-1, and one 60L LPV batch was formulated with Brenntag's Adju-Phos gel as a 'control'—for comparison of the product produced using the procedure as described in Example-1 and Brenntag's AlPhos gels. The aluminium phosphate gel was prepared at 18L scale using sterilized solutions & in sterile vessel and was transferred in sterile glass bottles for sterilization by autoclaving; this sterile gel was transferred to blending vessel for LPV blending.

Three Final Bulks of LPV were produced using in-house aluminium phosphate gel, with the following batch numbers (as mentioned in tables 6 & 7, under Example-5): LPV-1, LPV-2 and LPV-3. The 'reference' batch of LPV Final Bulk produced with Brenntag's Adju-Phos was given the number 'LPV-4'.

The lots of antigens used for formulation of LPV-1 and LPV-4 were the same, to enable comparison of impact of gel made prepared according to the present invention and that of Adju-Phos available commercially, made by Brenntag Biosector. The results of all qualitative & quantitative tests complied with the acceptance criteria for respective parameter, and thus confirm that the AlPhos Gel prepared according to the present invention produced the LPV lots which were highly comparable with that produced using the Adju-Phos of Brenntag, thus confirming the suitability of in-house AlPhos gel in making the vaccine preparations.

Similar to the LPV, three Final Bulks of LQV (D-T-P-Hib vaccine) were also produced using aluminium phosphate gel prepared according to the present invention, with the following batch numbers (as mentioned in tables 6 & 7, under Example-5): LQV-A, LQV-B and LQV-C. The results of all qualitative & quantitative tests complied with the acceptance criteria (same as that for LPV) for respective parameter, thus reconfirming that the gel prepared according to the present invention for blending of LQV lots were also highly consistent. These data reaffirm the suitability of AlPhos gel of the present invention in making the vaccine preparations.

All the lots of LPV and LQV produced as above were filled into glass vials in single (0.5 mL) dose 10-dose (5.0 mL) presentations and subjected to stability studies at real-time (2-8° C.) and accelerated (25±2° C.) temperature storage conditions. The test parameters were evaluated to check the stability were all complying with the specifications up to 3 months storage, when last tested, at both conditions for both vaccines; and the results of stability parameters tested on the Final Lots filled from LPV-1 and LPV-4 up to 9 months' time-point when stored at Real-time storage conditions are again comparable, indicating no change in any of the parameters tested due to change in the AlPhos gel source.

Hence the process of the present invention to prepare Aluminium-Phosphate gel using the unique process has proven to be easily reproducible, scalable and highly suitable for use in vaccine preparations as an adjuvant.

The invention claimed is:

1. A process for preparing an aluminum phosphate gel, comprising:
    admixing and stirring water and solutions of aluminum salt and alkaline phosphate salt at a pH between 3.0 and 4.0 to obtain the aluminum phosphate gel; and
    (ii) sterilizing the aluminum phosphate gel of step (i) by exposing the aluminum phosphate gel to a temperature in a range of 120-150° C. for a period of 30 to 90 minutes,
    wherein the aluminum phosphate gel has particles with a size distribution of d(50) in a range of 3.0 μm to 9.0 μm and a mean particle size less than 7 μm, and
    wherein the process is devoid of the steps of settling an aluminum phosphate suspension and removal of a supernatant.

2. The process of claim 1, wherein the aluminum salt solution is aluminum chloride and the alkaline phosphate salt solution is trisodium phosphate, wherein concentrations of each of the solutions of aluminum chloride and trisodium phosphate are in the range of 400 and 500 milliMolar (mM), preferably between 480 and 490 mM.

3. The process of claim 2, wherein the admixing and stirring of aluminum chloride solution and trisodium phosphate solution is carried out at least at 400 rpm, preferably between 500 and 600 rpm.

4. The process of claim 1, wherein the admixing and stirring in step (i) is carried out at room temperature or at a temperature between 20° C. and 25° C.

5. The process of claim 1, wherein the admixing and stirring in step (i) is carried out for a period of 10 to 60 minutes, preferably 35 to 55 minutes.

6. The process of claim 1, wherein the aluminum phosphate gel has a particle size distribution wherein d(90) is in a range of <15 μm, preferably 5 to 10 μm.

7. The process of claim 1, wherein the process is carried out in a closed system.

8. The process of claim 1, wherein the process is carried out at a pH range of 3.2 to 3.5 without addition of any other acid or alkali.

9. The process of claim 1, wherein a supernatant is not formed.

10. A process for preparing an aluminum phosphate gel, comprising:

admixing and stirring water and solutions of aluminum chloride and trisodium phosphate for 60 minutes, preferably between 35 to 55 minutes, to form the aluminum phosphate gel, and maintaining a pH of the aluminum phosphate gel between 3.0 and 4.0, preferably between 3.2 and 3.5; and (ii) sterilizing the aluminum phosphate gel of step (i) by exposing the aluminum phosphate gel to a temperature in a range of 120-150° C. for a period of 30 to 90 minutes, wherein the aluminum phosphate gel has particles with a size distribution of d(50) in a range of 3.0 μm to 9.0 μm and a mean particle size less than 7 μm, and wherein the process is devoid of the steps of settling an aluminum phosphate suspension and removal of a supernatant.

11. A method of preparing a vaccine composition comprising adsorbing one or more antigens on the aluminum phosphate gel formed from the process of any one of claims 1-10.

* * * * *